ary Examiner—Richard J. Gallagher

United States Patent [19]
Deli et al.

[11] 4,013,675
[45] Mar. 22, 1977

[54] N-(3-METHYL-5-ISOTHIAZOLYL)-2-METHYLPENTANAMIDE

[75] Inventors: Joseph Deli, Rockford, Ill.; Henry C. Stevens, Akron, Ohio

[73] Assignee: PPG Industries, Inc., Pittsburgh, Pa.

[22] Filed: May 5, 1975

[21] Appl. No.: 574,792

[52] U.S. Cl. .............................. 260/306.8 A; 71/90
[51] Int. Cl.² ........................................ C07D 275/02
[58] Field of Search ............................ 260/306.8 A

[56] References Cited
OTHER PUBLICATIONS

Robba et al., *Annales Pharmaceutique Francaises*, 22, 1964, No. 3, pp. 201–210.

*Primary Examiner*—Richard J. Gallagher
*Attorney, Agent, or Firm*—Robert J. Grassi

[57] ABSTRACT

Disclosed is the novel compound, N-(3-methyl-5-isothiazolyl)-2-methylpentanamide, which has herbicidal properties, particularly against broad leaf and grass weeds. It is usually formulated into an agricultural composition, optionally with 5-propionylamino-3-methylisothiazole.

1 Claim, No Drawings

N-(3-METHYL-5-ISOTHIAZOLYL)-2-METHYL-PENTANAMIDE

CROSS-REFERENCE TO RELATED APPLICATIONS

This application is related to the subject matter of Control of Weeds With 5-Propionylamino-3-methylisothiazole, Ser. No. 574,791, now U.S. Pat. No. 3,980,464 filed even date herewith.

BACKGROUND OF THE INVENTION

1. Field of the Invention

This invention relates to N-(3-methyl-5-isothiazolyl)-2-methylpentanamide, and its use as a herbicide, particularly as a broadleaf weed and grass weed herbicide.

2. Description of the Prior Art

Robba and Moreau, in *Annales pharmaceutique francaises*, 22, 1964, No. 3, pages 201–210, describe 5-propionylamino-3-methylisothiasole as a derivative formed from 5-amino-3-methylisothiazole, (a compound described by Adam et al. in U.S. Pat No. 2,871,243) and propionyl chloride. They nitrated the derivative at the 4 position of the isothiazole ring, to form 5-propylamino-4-nitro-3-methylisothiazole, which was inactive against *Trichononos vaginalis*, a pathogen causing infections of the human vagina. In U.S. Pat. No. 2,839,529, Adams et al. describe 5-amino-3-methylisothiazole itself as an intermediate for 5-(p-acetamidobenzenesulphonylamino)-3-methylisothiazole, a useful bactericide for *Escherichia coli*. Other workers, in the Journal of the Chemical Society, 1959, pages 3061 to 3071, describe the acetyl, dichloroacetyl and benzoyl derivatives of the 3-amino-5-methylisothiazole but give no uses for them. The chloroacetyl derivative, an analgesic, is listed in volume 59 of *Chemical Abstracts* column 2791 (1963). Slack et al., in U.S. Pat. No. 3.186,999, describe semi-carbazone, and thiocarbazone derivatives of 5-amino-3-methylisothiazole, which are active against pox viruses. In Japanese Pat. No. 39-5641/64, S. Kamio et al. (Chemical Abstract 59, column 2791a) describe monohalogenocarboxylic amides of isothiazole as useful intermediates for aminocarboxylic acid derivatives.

U.S. Pat. Nos.: 3,155,678, 3,393,992, 3,454,591, 3,541,108, 3,563,985, 3,622,593, and 3,692,795 describe certain cyanated, halogenated, benzoated, or urea substituted isothiazole derivatives as herbicides for certain weeds, or as fungicides for certain fungi.

SUMMARY OF THE INVENTION

In accordance with this invention there is provided N-(3-methyl-5-isothiazolyl)-2-methylpentanamide, a novel compound which has been discovered to have herbicidal activity against weeds, particularly, broadleaf, and grass weeds. Control of weeds with the compound is achieved by contacting the weed environment, either in a post or preemergence application.

DESCRIPTION OF THE PREFERRED EMBODIMENTS

The compound N-(3-methyl-5isothiazolyl)-2-methylpentanamide, also referred to as 5-(2-methylpentanoylamino)-3-methylisothiazole, is made by reacting the 2-methylpentanoylchloride with 5-amino-3-methyl isothiazole in the manner described by M. Robba and R. C. Moreau (*Annales pharmaceutique francaises*, 22, 1964, No. 3, pages 201–204) for making the 5-propionyl and 5-hexanoyl, -amino-3-methylisothiazoles.

The preferred method, however is the reaction of 2-methyl pentanoic anhydride with 5-amino-3-methylisothiazole, as described in Example I.

EXAMPLE I

5-Amino-3-methylisothiazole hydrochloride (6.0 grams, 0.040 mole) was added to a solution of 2.0 grams (0.05 mole) of sodium hydroxide in 25-milliliters of water. The dark oil which formed was extracted into two 25-milliliter portions of ethyl ether, which were combined and dried over magnesium sulfate. This solution was then filtered into a 250-milliliter reaction flask equipped with a magnetic stirrer, addition funnel, and condenser/drying tube, and 5.0 grams (0.50 mole) of triethylamine was added. The addition funnel was charged with 25-milliliters of an ethylether solution containing 9.4 grams (0.044 mole) of 2-methylpentanoicanhydride, which solution was slowly added to the stirred solution in the flask over a 20 minute period. After stirring overnight, 25-milliliters of water were added to the clear yellow solution and stirred for 30 minutes. The layers were separated, and the organic layer was dried over magnesium sulfate, filtered and subjected to vacuum to give an orange oil (9.7 grams). IR and NMR spectra indicated that the material was contaminated with acid and anyhdride. The sample was dissolved in 50-milliliters of aqueous sodium bicarbonate solution containing 5 weight percent sodium bicarbonate for 3 hours. The layers were then separated, and the ethyl ether phase was dried over magnesium sulfate, filtered, and subjected to vacuum drying at 60 degrees Centigrade to give 5.5 grams of clear amber liquid, which crystallized on standing. The crystals were digested with 25-milliliters of hexane and 30-milliliters of ether, cooled to minus 40° C and filtered to give 3.2 grams of tan crystals of N-(3-methyl-5-isothiazolyl)-2-methylpentanamide, which exhibited a melting-point range of 99° to 103° C after vacuum drying.

In lieu of 2-methylpentanoic anhydride, 2-methylpentanoylchloride, or 2-pentanoic acid (in the presence of a dehydrating agent) may be used in Example I.

Although a substantially pure product is generally desirable, it is not a necessity, because an impure product may also be used, especially when the desired N-(3-methyl-5-isothiazolyl)-2-methylpentanamide is the predominant compound. In some cases, the resulting product may contain as little as 0.1 weight percent and as much as 100 weight percent of the compound itself and still be acceptable, especially when used itself as a herbicide, or in a suitable formulation in which the impurities contained in the product do not interfere with the other ingredients of the formulations.

The reaction may be conducted in any suitable solvent, such as benzene or ether, but preferably it is catalyzed by the use of a suitable tertiary amine, e.g., trimethylamine, triethylamine, pyridine, or N,N-dimethylaniline, etc. The reaction may be permitted to take place at room temperature over several hours, or at a moderately advanced temperature for a shorter period of time. The purification of the desired product may be effected in any suitable manner, such as washing an organic-phase product with an acidic, neutral and/or alkaline aqueous washing media, subjecting the organic phase to vacuum drying to remove volatiles, and suitably crystallizing and possibly recrystallizing.

The novel compound N-(3-methyl-5-isothiazolyl)-2-methylpentanamide, also referred to as 5-(2-methylpentanoylamino)-3-methylisothiazole possesses effective herbicidal properties against weeds, notably broadleaf weeds and grass weeds. In this regard it has been discovered to be more active against certain weeds than the compound 5-propionylamino-3-methylisothiazole, which is disclosed (to also possess certain herbicidal qualities) in copending application, Control of Weeds With 5-Propionylamino-3-Methylisothiazole.

N-(3methyl-5-isothiazolyl)-2-methylpentanamide is more active than 5-propionylamino-3-methylisothiazole against weeds of the genera: Xanthium, Abutilon, Sesbania, Datura, Sorghum, Digitaria, Eschinochloa, and Gossypium. N-(3-methyl-5-isothiazolyl-2-methylpentanamide is more active than 5-propionylamino-3-methylisothiazole against the species: Xanthium pensylvanicum (common cocklebur), Abutilon theophrasti (velvetleaf), Sesbania spp. (coffeeweed), Datura stramonium (jimsonweed), Sorghum halepense (johnsongrass), Digitaria sanguinalis (crabgrass), and Echinochloa crusgalli (barnyardgrass).

Use of N-(3-methyl-5-isothiazolyl)-2-methylpentanamide as a herbicide against weeds, in particular broadleaf weeds, and grass weeds involves contacting the weeds, either prior to planting crops, or after the field is planted with crops, with a lethal (or herbicidal) amount of the compound, usually in the form of a suitable agricultural composition which contains the compound. The lethal (or herbicidal) dosage will of course vary with the size, number of weeds and their species, plant size, weather, soil and the crop planted. Effective herbicidal dosages are from 0.25 to 500 lbs. per acre, more normally 0.25 to 50 lbs. per acre (0.27 to 55 kilogram/hectare), and preferably under optimum conditions from 1 to 10 lbs. per acre (1.1 to 11 kilogram/hectare).

Preferably, treatment is by contacting the emerged weed with the compound, that is when the weeds protrude from the soil. If both crop plants and weeds are emerging, treatment is best made after emergence of both. A preferred method is to contact the weed foliage with the compound.

Weed control with this compound can be effective in crop land, especially crop lands of peanuts, rice, corn, wheat, or oats. By chosing the appropriate mode of application, it is possible to treat even those crops often too sensitive to the pentanamide. Although, cotton is not tolerant to N-(3-methyl-5-isothiazolyl)-2-methylpentanamide, it is possible to make a directed-spray application to a field of cotton, directing the spray towards the ground and the small, newly emerged weeds, and away from the leaves of the cotton plants. Application, in most instances, is made after crop plants have emerged and are somewhat more mature than the plants of the weed species to be controlled, and the application is preferably made only a short time after the emergence of weed seedlings. If necessary or desired, additional applications of the active ingredient may be made.

N-(3-methyl-5-isothiazolyl-2-methylpentanamide is particularly effective against broadleaf and grass weeds of the following genera: Brassica, Commelina, Sorghum, Setaria, Digitaria, Echinochloa, Chenopodium, Amaranthus, Sesbania, Cassia, Xanthium, Sida, Abutilon, Datura, Ipomoea, Gossypium, Avena, Medicago, and Oryza. The compound was found extremely effective against the species: Brassica kaber, Commelina spp., Sorghum halepense, Setaria magna, Digitaria sanguinalis, Echinochloa crusgalli, Avena fatua, Chenopodium album, Amaranthus retroflexus, Sesbania spp., Cassia obtusifolia, Xanthium pensylvanicum, Sida spinosa, Abutilon theophrasti, Datura stramonium, Ipomoea purpurea, and Ipomoea hederacea.

The following examples illustrate the herbicidal effectiveness of N-(3-methyl-5-isothiazolyl)-2-methylpentanamide.

EXAMPLE II

The tests described herein were conducted in the laboratory under laboratory conditions. A soil mixture of 3:1 silt loom soil to sand mixture was fertilized with 12-12-12 farm grade fertilizer at a rate of 75 lb/acre of total nitrogen (82.5 kilogram/hectare). This soil mixture was placed in flats (to a depth of about 2.5 inches), and seeds were then planted in accordance with a growth-time schedule of about 5 to 20 days in advance of the intended time for spraying with the herbicidal composition to insure that the emerging plant contained one or more true leaves. For example, broadleaf species such as lambsquarter were planted prior to weedy grasses such as johnson grass.

The planted seeds were as follows: Brassica kaber (mustard), Commelina spp. (dayflower), Sorghum halepense (johnsongrass), Setaria magna (giant foxtail), Digitaria sanguinalis (crabgrass), Echinochloa crusgalli (barnyardgrass), Avena fatua (wild oats), Chenopodium album (comon lambsquarter), Amaranthus retroflexus (redroot pigweed), Sesbania spp. (coffeeweed), Cassia obtusifolia (sicklepod), Xanthium pensylvanicum (common cocklebur), Sida spinosa (prickly sida, teaweed), Abutilon theophrasti (velvetleaf), Datura stramonium (jimsonweed), Ipomoea purpurea (tall morningglory), Ipomoea hederacea (ivyleaf morningglory), Medicago spp. (alfalfa), Lycopersicon esculentum (tomato), Beta vulgaris (sugar beets), Arachis hypogoea (peanut), Gossypium hirsutum (cotton), Oryza sativa L. (rice), Zea mays (corn), Triticum spp. (wheat), Avena spp. (oats), and Glycine max (soybeans). These constitute a good cross section of broadleaf and grass weeds.

Each section (4.63 square feet in area) was sprayed at a time when it had vigorous and good uniformity of growth with 20-milliliter portions of a formulation which contained a solvent mixture of 90 weight percent acetone, 8 weight percent methanol, 2 weight percent dimethylformamide, and the appropriate amount of the compound to give the desired application rate set forth in Table I. For application rates of 0.5 lb per acre (0.55 kilogram/hectare) the 20-milliliter portions contained 24.1 milligrams of the compound, for 1.0 lb/acre (1.1 kilogram/hectare) — 48.2 milligrams, and for 2.0 lb/acre (2.2 kilogram/hectare) — 96.4 milligrams of N-(3-methyl-5-isothiazolyl)-2-methylpentanamide.

After spraying the treated sections, these plants were allowed to grow under the usual controlled lab conditions. Observations were made daily, and the final plant observation was made 14 days after the spray treatment. The observations included all abnormal physiological responses such as stem bending, petiole curvature, epinasty, hyponasty, retardation, stimulation, root development, necrosis, and other related growth regulant characteristics.

These observations are shown in Table I, as weed control ratings, (based on the final observation), reported on a scale of 0 no control or effect, to 10 complete control or effect, that is the plant is killed. The abbreviations following the ratings indicate the type of injury or plant response; Ne-necrosis, R-retarded, Cl-chlorosis, and 0 is none.

TABLE I

EFFECT ON PLANTS CONTACTED AFTER EMERGENCE WITH N-(3-METHYL-5-ISOTHIAZOLYL)-2-METHYLPENTANAMIDE AT APPLICATION RATES OF 0.5, 1.0, AND 2.0 lb/acre

| Species | Application Rate | | |
|---|---|---|---|
| | 2.0 lb/acre | 1.0 lb/acre | 0.5 lb/acre |
| BroadLeaf Weeds | | | |
| Datura stramonium (jimsonweed) | 10:Ne | 10:Ne | 7:RCl |
| Brassica kaber (mustard) | 10:Ne | 10:Ne | 9:Ne |
| Amaranthus retroflexus (redroot) | 10:Ne | 10:Ne | 9:Ne |
| Chenopodium album (lambsquarter) | 10:Ne | 10:Ne | 10:Ne |
| Sida spinosa (prickly sida, teaweed) | 6:Cl | 6:Cl | 4:Cl |
| Cassia obtusifolia (sicklepod) | 10:Ne | 10:Ne | 8:Ne |
| Abutilon theophrasti (velvetleaf) | 10:Ne | 6:NeR | 5:NeR |
| Sesbania spp. (coffeeweed) | 10:Ne | 8:NeR | 4:Ne |
| Xanthium pensylvanicum (common cocklebur) | 10:Ne | 10:Ne | 9:Ne |
| Ipomoea purpurea (tall morningglory) and Ipomoea hederacea (ivyleaf morningglory) | 9:Ne | 5:NeCl | 4:Cl |
| Commelina spp. (dayflower) | 8:NeR | 6:NeR | 6:NeR |
| Grass Weeds | | | |
| Sorghum halepense (johnsongrass) | 8:Ne | 6:NeR | 2:Ne |
| Setaria magna (gaint foxtail) | 8:Ne | 9:Ne | 8:Ne |
| Digitaria sanguinalis (crabgrass) | 7:NeR | 6:NeR | 2:Ne |
| Echinochloa crusgalli (barnyardgrass) | 9:Ne | 5:NeR | 3:NeR |
| Avena fatua (wild oats) | 4:Ne | 3:Ne | 2:NeR |
| Crops | | | |
| Medicago spp. (alfalfa) | 6:NeR | 8:Cl | 6:Cl |
| Lycopersicon esculentum (tomato) | 10:Ne | 9:NeCl | 6:Cl |
| Beta vlugaris (sugar beets) | 10:Ne | 9:Ne | 9:Ne |
| Arachis hypogoea (peanuts) | 3:Cl | 3:Cl | 1:Cl |
| Gossypium hirsutum (cotton) | 10:Ne | 9:Ne | 5:Ne |
| Glycine max (soybeans) | 10:Ne | 8:Ne | 4:Cl |
| Oryza sativa L. (rice) | 2:Ne | 2:Ne | 0:0 |
| Zea mays (corn) | 2:Ne | 2:Ne | 1:Ne |
| Triticum spp. (wheat) | 1:NeR | .:0 | 0:0 |
| Avena spp. (oats) | 2:NeR | 2:NeR | 1:Ne |

In comparable tests, 3-amino-5-methylisothiazole, 3-acetylamino-5-methylisothiazole, and 3-benzamido-5-methylisothiazole showed very little activity.

EXAMPLE III

The following comparative test shown in Table II shows the greater activity of N-(3-methyl-5-isothiazolyl)-2-methylpentanamide against certain genera of weeds and in particular against certain weed species, than the known compound 5-propionylamino-3-methylisothiazole. This test was conducted under similar laboratory conditions as that of Example II described previously. The compounds are applied at an application rate of 2.0 lbs/acre (2.2 kilograms/hectare). The results of this test are shown in Table II, the ratings of which have the same significance as in Table I.

TABLE II

COMPARATIVE POSTEMERGENT EVALUATION AT 2.0 lbs/acre

| Species | Compounds | |
|---|---|---|
| | N-(3-methyl-5-isothiazolyl)-2-methylpentanamide | 5-propionylamino-3-methylisothiazole |
| BroadLeaf Weeds | | |
| *Datura stramonium* (jimsonweed) | 10:Ne | 9:NeR |
| *Abutilon theophrasti* (velvet leaf) | 10:Ne | 8:Ne |
| *Sesbania spp.* (coffeeweed) | 10:Ne | 8:Ne |
| *Xanthium pensylvanicum* (common cocklebur) | 10:Ne | 6:Ne |
| *Ipomoea purpurea* (tall morningglory) and | | |
| *Ipomoea hederacea* (ivyleaf morningglory) | 9:Ne | 5:Ne |
| Grass Weeds | | |
| *Sorghum halepense* (johnsongrass) | 8:Ne | 1:Ne |
| *Digitaria sanguinalis* (crabgrass) | 7:Ne | 3:Ne |
| *Echinochloa crusgalli* (barnyardgrass) | 9:Ne | 3:Ne |
| *Avena fatua* (wild oats) | 4:Ne | 2:Ne |
| *Gossypium hirsutum* (cotton) | 10:Ne | 8:Ne |

These results show that the N-(3-methyl-5-isothiazolyl)-2-methylpentanamide is more active against weeds of the genera Datura, Abutilon, Sesbania, and Xanthium and Gossypium, particularly at these low application rates, and in particular against the species shown in Table II, than is 5-propionylamino-3-methylisothiazole.

When applying the compound N-(3-methyl-5-isothiazolyl)-2-methylpentanamide, it is usually formulated as an agricultural formulation. The compound itself, or together with other herbicides, pesticides, etc., or 5-propionylamino-3-methylisothiazole may be formulated as a granule of relatively large size, as a powdery dust, as a wettable powder, as an emulsifiable concentrate, as a solution, etc., or other agriculturally suitable composition depending upon the mode of application desired. For preemergence application to control vegetation, the compound is usually applied to the area as a spray, dust, or granule; for postemergence application to remove an established weed, a spray or dust is generally employed. In all of these formulations, the active ingredient is diluted with an inert carrier either a solid or liquid diluent. The formulations may contain as little as 0.1 percent or as much as 99 percent or more by weight of the compound itself as an active ingredient.

The compound, N-(3-methyl-5-isothiazolyl)-2-methylpentanamide, may be formulated as a simple solution, in solvents which completely solubilize the compound at the desired concentrations, e.g., acetone, xylene, or other organic solvents. It may be formulated in aerial spray formulations which comprise relatively coarse particles coated with the compound, or in pressurized spray formulations, e.g., aerosols, which use low boiling dispersant solvents such as Freon.

The compound may be formulated as in the above mentioned formulations with other suitable agricultural ingredients such as fertilizers, nematocides, pesticides, or other herbicides which are compatible with one another, which are nontoxic to the desired vegetation, but which are effective against other weeds, pests, nematodes and their eggs, fungi, and bacteria, so as to form a suitable agricultural composition which enables ridding the treated area of several undesirable species with a single application.

The compound may be formulated as simple solutions, aerial sprays, or aerosols in combination with 5-propionylamino-3-methylisothiazole to increase its effectiveness. These formulations may, of course, contain other pesticides, herbicides, fertilizers, nematocides, which are compatible with one another, and which are nontoxic to desired vegetation.

Dust formulations of N-(3-methyl-5-isothiazolyl)-2-methylpentanamide may be used. These are mixtures of the active compound with finely divided solids such as talc, altapulgite, clay, kieselguhr, and other organic and inorganic solids which act as dispersants and carriers for the compound. The finely divided solids have an average particle size of less than about 50 microns. A typical dust formulation will contain from 1.0 to 10.0 parts by weight of N-(3-methyl-5-isothiazolyl)-2-methylpentanamide to 99.0 to 90.0 parts by weight of talc.

The compound when formulated as a dust may be combined with other suitable agricultural ingredients such as herbicides of urea, thiocarbamates, etc., pesticides, nematocides, fertilizers, bactericides, fungicides, which are compatible with one another, and which are nontoxic to the desired vegetation. These agricultural compositions when applied rid the area of many undesirable pests, etc., so that time and money are saved. In these formulations the agricultural compositions may contain at least from 1.0 to 10.0 parts by weight of N-(3-methyl-5-isothiazolyl)-2-methylpentanamide.

The compound may be formulated in a dust composition which contains 5-propionylamino-3-methylisothiazole. These compositions may contain at least from 1.0 to 10.0 parts by weight of the N-(3-methyl-5-isothiazolyl)-2-methylpentanamide. Of course these dust compositions may also contain in various ratios other compatible herbicides, pesticides, bactericides, nematocides, nematode egg hatching ingredients, fungicides, or fertilizers which will enhance the effectiveness of the dust compositions to remove one or more pests from the treated area.

Wettable powders, another type of formulation, are finely divided particles which disperse in water or other liquids. The wettable powder is applied to the soil, seed, or plant as a dry dust or as a water or other liquid emulsion.

Typical wettable powder carriers are Fuller's earth, Kaolin clays, silicas, and other highly absorbent, readily wet inorganic diluents. Wettable powders normally contain about 5 to 80 weight percent of the active ingredient, depending on the absorbency of the carrier, and usually contain a small amount of a wetting, dispersing, or emulsifying agent to facilitate dispersion.

For example, a useful wettable powder formulation comprises about 80.8 parts of N-(3-methyl-5-isothiazolyl)-2-methylpentanamide, 17.9 parts of Palmetho clay and 1.0 part of sodium lignosulfate and 0.3 parts of sulfonated aliphatic polyester as wetting agents. Another useful wettable-powder formulation contains 50 weight percent of the active amide, about 40 weight percent of hydrated silica, and about 10 weight percent of other ingredients such as emulsifiers. Such a powder is produced by mixing the desired ingredients and milling them to a suitably fine particle size, such as 1 to 200 microns, and preferably under 74 microns.

The wettable powder formulations may contain other compatible agriculturally suitable compounds such as herbicides, fertilizers, pesticides, bactericides, fungicides, or other ingredients which serve to enhance the growth of crops.

The wettable-powder formulation is mixed with a suitable quantity of water, such as 4 to 20 gallons of water per pound of formulation, and then applied to the crop land, by the use of aerial or land-based spraying equipment, at a suitable rate such as 10 to 100 gallons per acre. The rate of spraying is co-ordinated with the strength of the material to be applied so as to give the desired weight of active ingredient per unit of area.

Other formulations particularly for postemergent applications are emulsifiable concentrates. These are homogeneous liquid or paste compositions which are dispersible in water or other liquids. They may consist entirely of N-(3-methyl-5-isothiazolyl)-2-methylpentanamide and a liquid or solid emulsifying agent, or they may also contain a liquid carrier, such as xylene, heavy aromatic naphthas, or other nonvolatile organic solvents. These emulsifiable concentrates are dispersed in a liquid carrier, e.g., water, and generally are applied as a spray to the area or plant to be treated. The weight per cent of N-(3-methyl-5-isothiazolyl)-2-methylpentanamide in these concentrates varies with the manner of application, but generally is from 0.5 to 95 percent.

Representative wetting, dispersing and emulsifying agents for the agricultural formulations are alkyl and alkylaryl sulfonates and sulfates, and their alkali salts; polyethylene oxides, sulfoxided oils, fatty acids esters of polyhydric alcohols, and other surface active agents, e.g., Tween 20, a commercial surfactant. If used, the surfactant would vary from 0.25 to 15 weight percent of the composition.

These emulsifiable formulations may also include other useful agricultural materials such as nematocides, pesticides, bactericides, fungicides, and herbicides which are non-toxic to the desired vegetation, but which are effective against other weeds, pests, and nematodes, their eggs, fungi, and bacteria so that one application will serve to rid the area of several undesirable species.

In all these formulations, other combinations of the compound are those with ureas, areas, thiolcarbamates, carbamates, which increase the useful herbicidal spectrum of the compound, and reduce the number of applications required by husbandmen and others who require use of these compounds to assist the healthful growth of crops. It may be used in combination with fertilizers, particularly those used in foliage applications, provided of course that the composition formulation is such that N-(3-methyl-5-isothiazolyl)-2-methylpentanamide is not hydrolyzed, e.g., the pH conditions are maintained between 2–10, preferably between 5 and 8.

When the compound N-(3-methyl-5-isothiazolyl)-2-methylpentanamide is applied in the form of a suitable agricultural composition, the application rate of such formulation is such that the herbicidal dosage of the compound itself is between 0.25 to 500 lbs. per acre (0.27 to 550 kilograms/-hectare). Generally, the rate is from 0.25 to 50 lbs. per acre (0.27 to 55 kilograms/hectare), but preferably from 1 to 10 lbs. per acre (1.1 to 11 kilograms/hectare) under optimum conditions.

While the invention has been described with reference to specific details for certain illustrative embodiments, it is not intended that it shall be limited except in so far as such details appears in the accompanying claims.

We claim
1. N-(3-methyl-5-isothiazolyl)-2-methylpentanamide.

* * * * *